United States Patent [19]

Clementi et al.

[11] Patent Number: 5,000,553

[45] Date of Patent: Mar. 19, 1991

[54] APPARATUS FOR THE ALIGNMENT OF A LASER BEAM INSIDE AN ARTICULATED TUBULAR ARM

[75] Inventors: Gabriele Clementi; Leonardo Masotti; Francesco Muzzi, all of Florence, Italy

[73] Assignee: El. En s.r.l., Florence, Italy

[21] Appl. No.: 467,642

[22] Filed: Jan. 19, 1990

[30] Foreign Application Priority Data

Feb. 9, 1989 [IT] Italy .................................. 9336 A/89

[51] Int. Cl.⁵ ............................ G02B 5/08; H01S 3/10
[52] U.S. Cl. ..................................................... 350/486
[58] Field of Search .............................. 350/486, 138; 219/121.79

[56] References Cited

FOREIGN PATENT DOCUMENTS 0073003  6/1980  Japan ................................. 350/486

Primary Examiner—Bruce Y. Arnold
Assistant Examiner—Rebecca D. Gass
Attorney, Agent, or Firm—McGlew & Tuttle

[57] ABSTRACT

The articulated arm of a laser equipment comprises at least an articulation with a corresponding mirror in a fixed and non-adjustable position with respect to said articulation. At least one of the sections of the articulated arm converging into said articulation is engaged with the articulation in an angularly adjustable manner. In this way, with an angular adjustment of said arm section a perfect alignment of the laser beam in the tubular arm can be achieved.

8 Claims, 2 Drawing Sheets

APPARATUS FOR THE ALIGNMENT OF A LASER BEAM INSIDE AN ARTICULATED TUBULAR ARM

The invention refers to an apparatus for the alignment of a laser beam inside an articulated tubular arm of a laser equipment for use, for example but not exclusively, in surgery.

In the CO2-operated lasers for surgical use, and in other types of laser, for example e.g. in excimer lasers, the features the laser beam are such as not to allow injection thereof in an optical fibre. In particular, in the lasers for surgery use, the wave length of the emitted radiation is too high and its transmission into an optical fibre is not possible, while in the excimer lasers the beam power may reach too high values and causes therefore the breaking of the fibre.

Accordingly, in apparatus making use of laser sources of the above mentioned type, for the propagation and guide of the laser beam there are employed arms made up of a plurality of sections articulated to each other, with mirrors in correspondence of the articulations to convey the laser beam from the source to the utilization point. To align the mirrors and thus achieve a path of the laser beam along the axis of the articulated arm, said mirrors are currently disposed on mirror-holders equipped with adjustment screws by which it is possible to obtain the correct positioning of the reflection plane of each mirror.

With this kind of adjustment, when the inclination of the mirror is changed, there is also changed the position of the mirror itself with respect to the articulation. This modification of the position causes an error of coaxiality, in the sense that the laser beam, sent back by the mirrors, is parallel to the arm axis but not coincident therewith. This brings about diaphragm effects during the various passages through the openings located along the beam path.

The object of the invention is to provide an apparatus for the alignment of the laser beam inside a conduit formed in the articulated tubular arm, which overcomes the above mentioned drawbacks.

This and other objects, which will become apparent to those skilled in the art by a reading of the following description, are achieved in practice by an apparatus of the above mentioned type, characterized in that the mirror is fixed with respect to the relevant articulation, and that at least one of the sections of the articulated tubular arm converging in said articulation is engaged with the same articulation in an angularly adjustable manner. The mirror retains therefore its position with respect to the articulation during the alignment operations, said position being obtained by machine working with very close tolerances, while the adjustment is carried out by acting exclusively on the section of the articulated tubular arm in order to determine the correct inclination with respect to the articulation and thus to the mirror. By this adjustment it is possible to obtain a perfect coaxiality of the laser beam inside the tubular conduit formed in the articulated tubular arm.

In a practical embodiment of the invention, the angularly adjustable section is engaged through a flange with a bush solid to said articulation, means of adjustment and mutual locking being provided acting between said flange and said bush. Advantageously, said mutually locking means may comprise a set of clamping screws which pass through holes of said flange and are engaged in corresponding threaded holes of said bush, while said adjustment means may comprise a set of adjustment screws engaging in corresponding holes of said flange and cooperating with said bush to adjust the mutual inclination of the axes of the bush and of the section of the articulated tubular arm to which said flange is solid. The mutually locking means may further comprise a threading in said bush on which the flange is made to engage by a threading formed in the peripheral zone.

To reduce the wear, said adjustment screws advantageously cooperate with the surface of a washer member disposed between said flange and a shoulder inside said bush.

A further object of the invention is that of maintaining the perfect coaxiality of the laser beam obtained by the described apparatus even during the use of the laser equipment by reducing the bending stresses on the said section of said articulated tubular arm and the dynamic stresses onto the articulation. To achieve this object, said section is suspended by means of a filiform elastic element, e.g. a steel wire, coupled with one end through a restrained joint in correspondence of the articulation facing the laser source, and engaged at the opposite end to said section of said arm in the vicinity of the next articulation. The filiform element is advantageously elastically pre-loaded so as to result constantly bending stressed.

In a possible embodiment said filiform element is engaged to said section of the articulated tubular arm by means of a bracket, said bracket being fitted with clearance on said section.

The invention will be better understood by the following description and the attached drawing, which shows a practical, not limiting example of the same invention. In the drawing.

Figure 1:
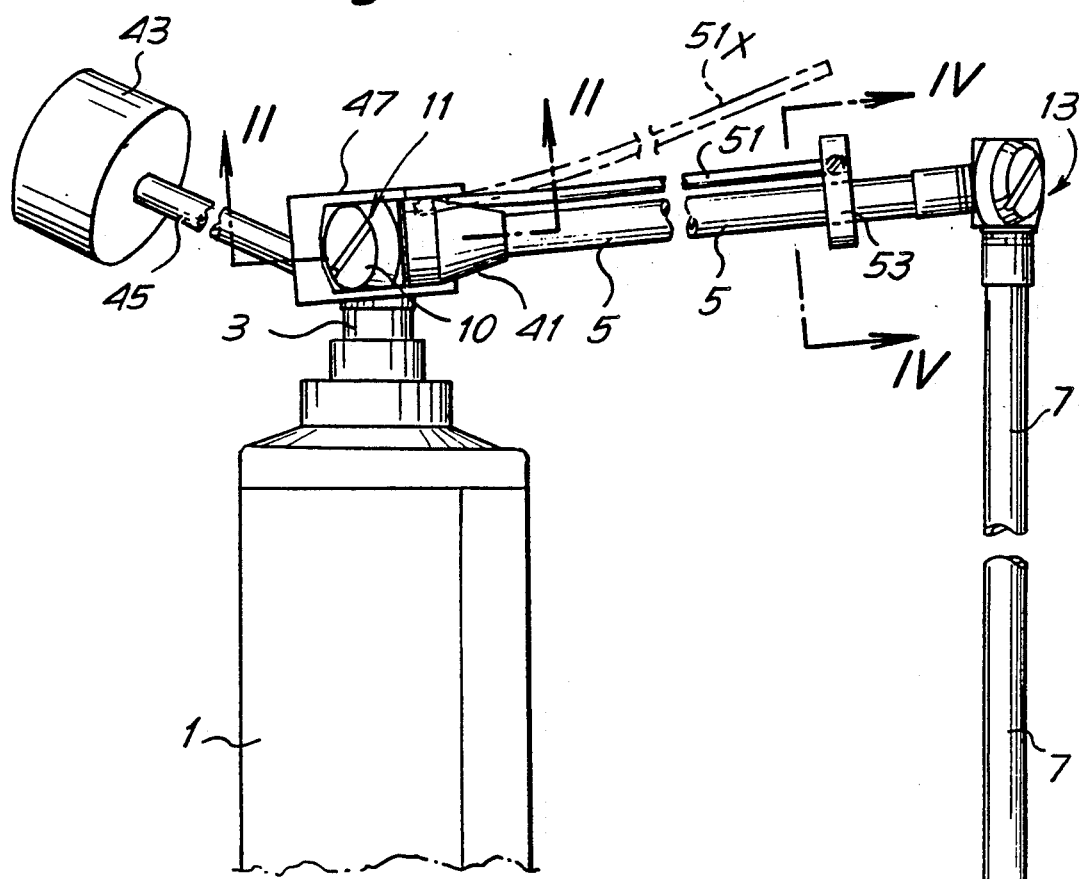
FIG. 1 shows a schematic side view of an arm equipped with the apparatus according to the invention.

Referring now to FIG. 1, numeral 1 indicates the housing in which the laser source is held. The beam generated by the source is directed into a conduit having a first section 3 and a plurality of further sections 4 (orthogonal to the plane of the drawing of FIG. 1), 5, 7, 9 articulated to each other in correspondence of articulations 11, 13, 15, 16, wherein reflecting mirrors are located able to divert the beam along the axis of the various sections making up the articulated arm.

Particularly crucial is the alignment of the beam in correspondence of articulation 11, as the path that the beam must follow from this articulation to the outlet 9A of last section 9 of the conduit is particularly long, especially within arms having many articulations such as the one herein illustrated.

Figure 2:
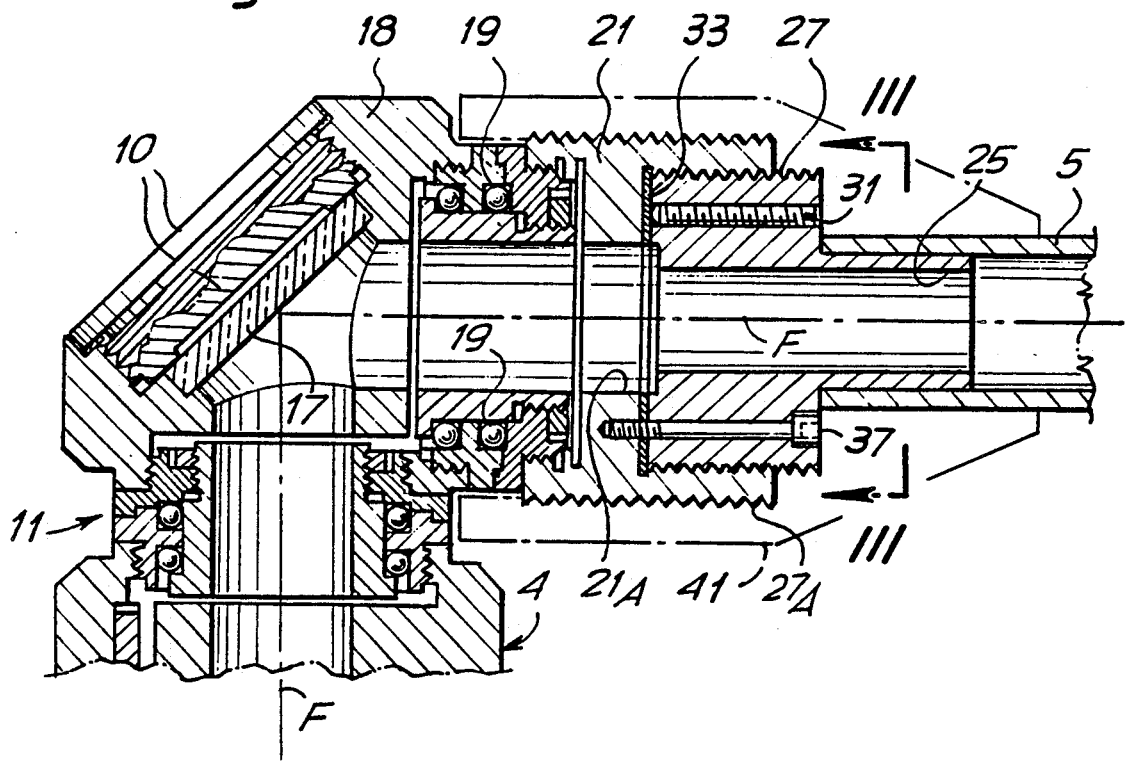
FIG. 2 shows a longitudinal section of the apparatus taken on line II—II of FIG. 1

FIG. 2 shows a local section of articulation 2 which joins sections 4 and 5 of the tubular arm. In this figure a mirror-holder 10 is shown with the relevant mirror 17 which diverts the beam F coming from the laser source through 90° on order to direct it into section 5 of the articulated arm. The mirror-holder 10 is supported by an element 18 which forms the body of articulation 11, on which the sections 4 and 5 of the articulated arm are pivotally engaged. To allow section 5 to rotate about its own axis, bearings 19 (of a type known per se) are provided allowing the relative rotation between element 18 and bush 21 to which the section 5 of the articulated tubular arm is engaged as described below.

Figure 3:
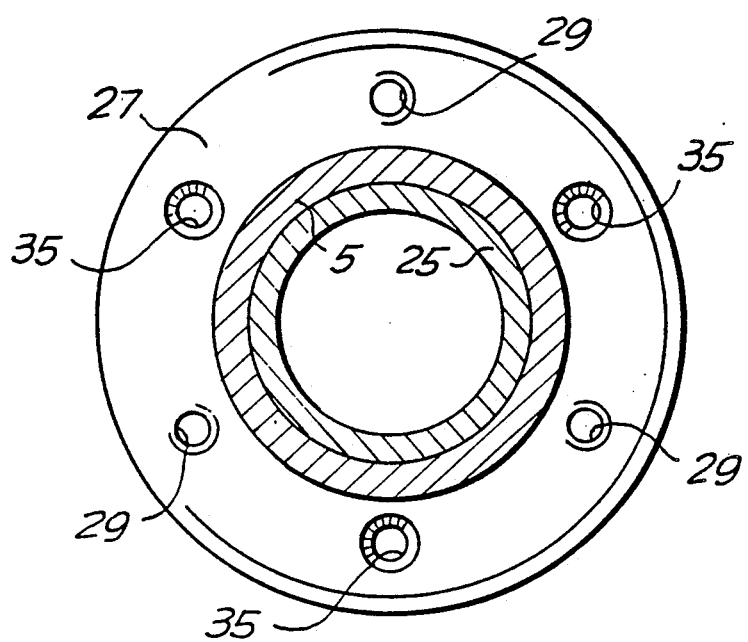
FIG. 3 shows a local section on line III—III of FIG. 2.

The mirror-holder 10 and relevant mirror 17 are rigidly engaged to the element 18 without any possibility of adjustment, contrary to what is provided in the apparatus of traditional type wherein the mirror-holder can be adjusted in position by suitable setting screws. According to the present invention, vice-versa, it is possible to adjust the position of section 5 of the tubular arm with respect to element 18 and relevant mirror. The position adjustment of section 5 allows a perfect coaxiality to be achieved between section 5 and laser beam F. In fact, during this adjustment, the position of the mirror does not vary, but it does vary only the inclination of section 5 of the arm with respect to mirror 17 thereby avoiding errors of coaxiality. To allow the adjustment, the section 5, at its terminal end for the engagement with the bush 21, is rigidly coupled to a sleeve 25 provided with a flange 27. The flange 27 has a first set of three threaded holes 29 (FIG. 3) forming 120° to each other, in which screws 31 engage which push against a washer 33 disposed between flange 27 and an inner shoulder 21A of bush 21. Said washer is advantageously made of hardened material to reduce the wear caused by the tips of the screws 31 pressing thereagainst. The flange 27 is provided with a further set of three through holes 35, also disposed at an angle of 120° to each other, which allow screws 37 to go through and engage in corresponding threaded holes formed in the inner shoulder 21A of bush 21.

The screws 37 are intended to lock the sleeve 25, and thus the section 5 of the articulated arm, to bush 21, while pressing screws 31 allow the inclination of flange 24, and thus of section 5, to be adjusted with respect to mirror 17. By acting on the pressing screws 31, therefore, there is obtained the perfect coaxiality of the laser beam F with respect to the axis of section 5; once such coaxiality is obtained, the section 5 itself is locked by the screws 37 through flange 27. The adjustment does not involve any variation of the position of mirror 17 and, therefore, does not introduce any error of coaxiality. The connection between flange 17 and bush 21 is further ensured by an outer perpheral threading 27A of flange 27, which engages into a corresponding threading of bush 21. The clearance between the threads is sufficient to allow the adjustment of the inclination between the articulation and section 5.

The locking screws 37 and the pressing screws 31 may be covered, during the use of the apparatus, with a frustoconical cap 41 (FIG. 1) fitted on section 5 and screwed on the outer threading 27A of flange 27.

The apparatus according to the invention is particularly advantageous when used for the alignment in correspondence of the first and/or the second articulation of the articulated tubular arm, as the errors of alignment occurring in this articulation are particularly detrimental due to the fact that they affect the whole arm length. However, the same alignment apparatus can be utilized also for the subsequent articulations.

When using the laser equipment, the articulated arm 5, 7, 9 is kept almost balanced by means of a counterweight 43 supported by a stem 45 engaged through a block 47 solid to a sleeve, not shown, fitted on the arm section 4 which is closest to the housing 1 of the laser source. Due to the inertia of the counterweight, when the operator acts on the articulated arm 5, 7, 9 he induces, bending stresses, especially in section 5, which may cause a deformation of the same section and thus an error in the laser beam alignment. Moreover, the sudden movements of the articulated arm may cause sudden dynamic loads on the articulation bearings.

Figure 4:
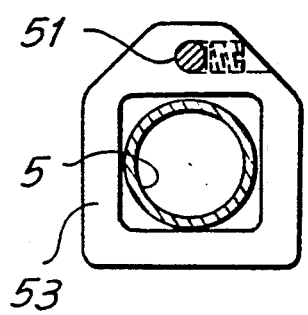
FIG. 4 shows a local section on line IV—IV of FIG. 1.

After having carried out the perfect alignment of section 5 of the articulated tubular arm, in order to prevent the laser beam F from coming out of alignment owing to a too sudden manoeuvre of the same arm, according to the invention there is provided a special elastic suspension system. Said system comprises a music wire or round bar 51 made of steel or other suitable material, of proper diameter, typically 5-6 mm, with one end restrained in block 47 for the support of counterweight 43. At the opposite end, the wire 51 is engaged to a bracket 53 (see in particular FIG. 4) fitted with some clearance on section 5 of the articulated tubular arm. Advantageously, the wire 51 is elastically pre-loaded to take up, when load-free at one end, an arcuate configuration as shown by in dashed line in FIG. 1 and designated by 51X. As a consequence, any bending stress induced on section 5 by a tensile load through the next section 7 (the operator holds always the last portion of the articulated tubular arm) is discharged through the wire 51 which, being pre-loaded, prevents or, anyhow, reduces substantially the deformation of section 5 of the tubular arm. Moreover, the elasticity of wire 51 prevents sudden shock loads on the bearings of articulation 11, which shock loads or kickbacks may cause mechanical damages and/or misalignments like those occurring in the rigid systems presently known. Advantageously, the sleeve (not shown) to which block 47 is solid, is fitted on the arm section 4 with the interposition of an anti-friction ring which allows relative rotation movements of the counterweight 43 about the axis of section 4.

It is understood that the drawing shows an exemplification given only as a practical demonstration of the invention as this may vary in the forms and dispositions without, nevertheless, coming out from the scope of the idea on which the same invention is based.

We claim:

1. An apparatus for the alignment of a laser beam inside an articulated tubular arm of a laser equipment, said arm comprising at least an articulation with a mirror for reflecting the laser beam, characterized in that said mirror (17) is fixed with respect to said articulation, and that at least one (5) of the sections (4, 5) of the articulated tubular arm converging into said articulation is engaged with said articulation in an angularly adjustable manner.

2. Apparatus according to claim 1, wherein said angularly adjustable section (5) is engaged through a flange (27) with a bush (21) solid to said articulation, means (31, 37) for mutually adjusting and locking being provided between said flange and said bush.

3. Apparatus according to claim 2, wherein said flange (27) is screwed on said bush (21), the clearance on the threading (27A) allowing the mutual angular adjustment of said flange and said bush.

4. Apparatus according to claim 2, wherein said means for mutually adjusting and locking comprise a set of locking screws (37) going through the holes (35) of said flange (27) and engaging in corresponding threaded holes provided in said bush (21), and wherein said adjustment means comprise a set of adjustment screws (31) which engage in corresponding holes (29) of said flange (27) and cooperate with said bush (21) to adjust the mutual inclination of the axes of the bush (21) and of the section (5) of the articulated tubular arm to which said flange (27) is solid.

5. Apparatus according to claim 4, wherein said adjustment screws (31) cooperate with the surface of a washer member (33) disposed between said flange (27) and an inner shoulder (21A) of said bush (21).

6. Apparatus according to claim 1, wherein said section (5) of said articulated tubular arm is suspended by means of an elastic element (51) having straight development, restrained with a first end in correspondence of the articulation (11) facing the laser source and engaged with the opposite end to said section (5) in the vicinity of the adjoining articulation (13).

7. Apparatus according to claim 6, wherein said elastic element (51) is elastically pre-loaded so as to be constantly bending-stressed.

8. Apparatus according to claim 6, wherein said elastic element (51) is engaged to said section (5) of the articulated tubular arm by means of a bracket (53), said bracket being fitted with clearance on said section (5).

* * * * *